United States Patent [19]

Ehrenkranz

[11] Patent Number: 5,222,809
[45] Date of Patent: Jun. 29, 1993

[54] METHOD AND APPARATUS FOR OBTAINING THE CORE BODY TEMPERATURE OF AN INFANT

[76] Inventor: Joel R. L. Ehrenkranz, Millbrook Rd., New Vernon, N.J. 07976

[21] Appl. No.: 802,629

[22] Filed: Dec. 5, 1991

[51] Int. Cl.$^5$ .................. G01K 11/12; G01K 13/12; G01K 1/14
[52] U.S. Cl. .................. 374/141; 128/771; 128/736; 374/157; 374/162
[58] Field of Search ............... 374/141, 157, 160, 162; 128/771, 760, 761, 736; 116/207, 216; 73/863.52

[56] References Cited

U.S. PATENT DOCUMENTS

| | | | |
|---|---|---|---|
| Re. 33,686 | 9/1991 | Parrish | 128/736 |
| 2,271,254 | 1/1942 | De Witt | 374/157 |
| 2,610,629 | 9/1952 | Hawkins | 128/760 |
| 2,716,342 | 8/1955 | Ween et al. | 374/157 |
| 3,351,050 | 11/1967 | Naftolin | 128/2 |
| 3,586,041 | 6/1971 | Monestere | 137/525 |
| 3,711,871 | 1/1973 | Sherin | 4/110 |
| 3,811,136 | 5/1974 | Whitney | 4/110 |
| 3,830,107 | 8/1974 | Linzer | 73/421 |
| 3,878,571 | 4/1975 | Seeley | 4/110 |
| 3,918,433 | 11/1975 | Fuisz | 128/2 |
| 3,928,875 | 12/1975 | Persson | 4/110 |
| 4,064,760 | 12/1977 | Benjamin | 73/421 |
| 4,094,020 | 6/1978 | Franklin | 128/294 |
| 4,109,530 | 8/1978 | Kim | 73/427 |
| 4,211,749 | 7/1980 | Kantner | 422/102 |
| 4,238,448 | 12/1980 | Salvadori et al. | 422/58 |
| 4,241,017 | 12/1980 | Balistreri et al. | 422/58 |
| 4,387,726 | 6/1983 | Denard | 128/760 |
| 4,408,905 | 10/1983 | Ehrenkranz | 374/141 |
| 4,457,314 | 7/1984 | Knowles | 128/760 |
| 4,466,445 | 8/1984 | Abrams | 128/736 |
| 4,492,258 | 1/1985 | Lichtenstein | 141/1 |
| 4,494,581 | 1/1985 | Gordon | 4/141 |
| 4,564,299 | 1/1986 | Ehrenkranz | 374/157 |
| 4,569,090 | 2/1986 | Muller | 4/144 |
| 4,761,379 | 8/1988 | Williams et al. | 435/296 |
| 4,769,215 | 9/1988 | Ehrenkranz | 422/58 |
| 4,846,818 | 7/1989 | Keldahl et al. | 128/761 |
| 4,846,819 | 7/1989 | Welch | 128/761 |
| 4,911,698 | 3/1990 | Wapner | 128/761 |
| 5,049,144 | 9/1991 | Payton | 128/761 |

*Primary Examiner*—Thomas B. Will
*Assistant Examiner*—Diego F. Gutierrez

[57] ABSTRACT

A method and apparatus for measuring the core body temperature of infants or persons without volitional bladder control utilizing minimal urine volume. The device employs a readily deployed collection surface contiguous with a sump or reservoir into which the collected urine contacts a superabsorbent powder. Affixed to the reservoir is a peak temperature sensor for indicating the maximum temperature of the urine and thereby the core body temperature of the donor.

8 Claims, 2 Drawing Sheets

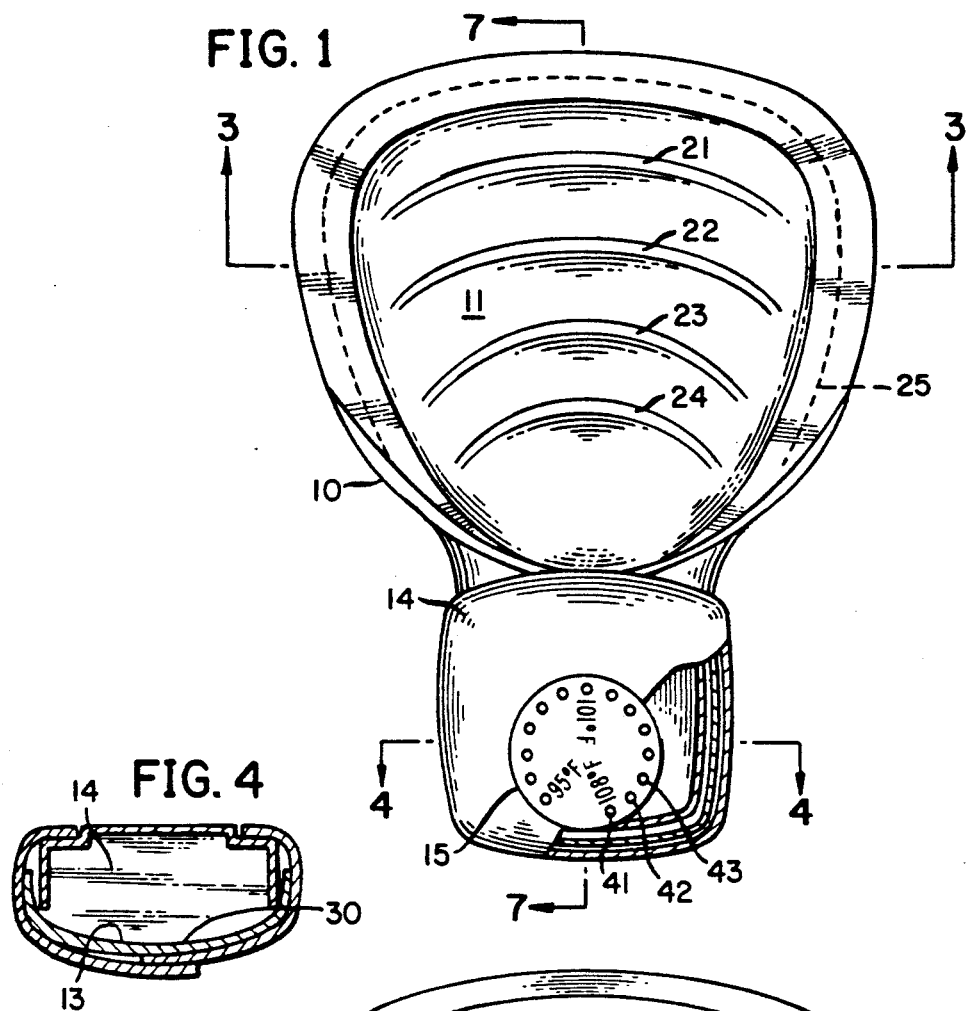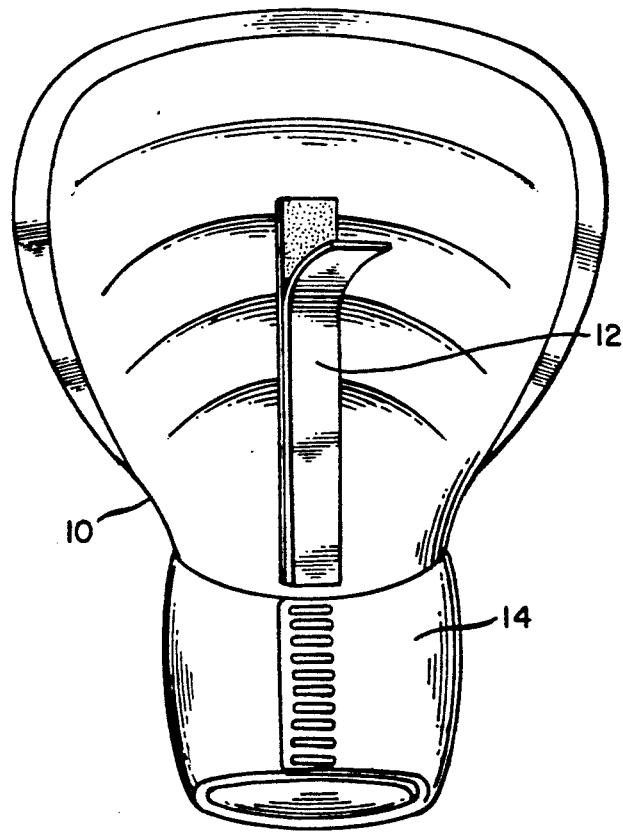

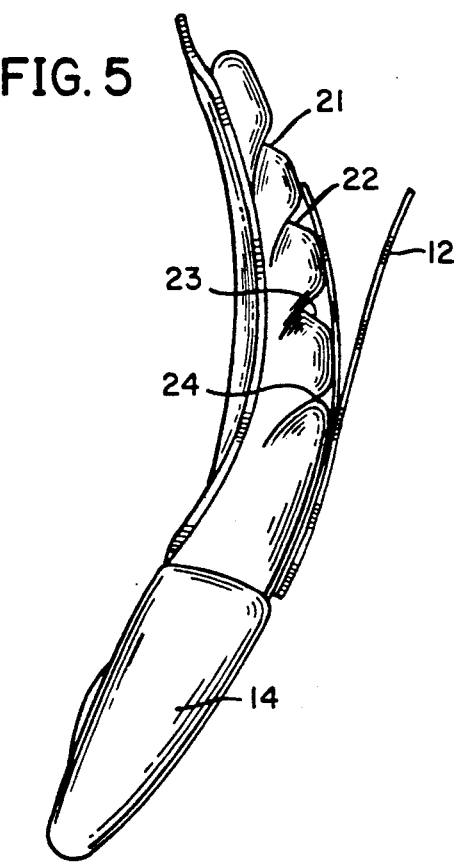
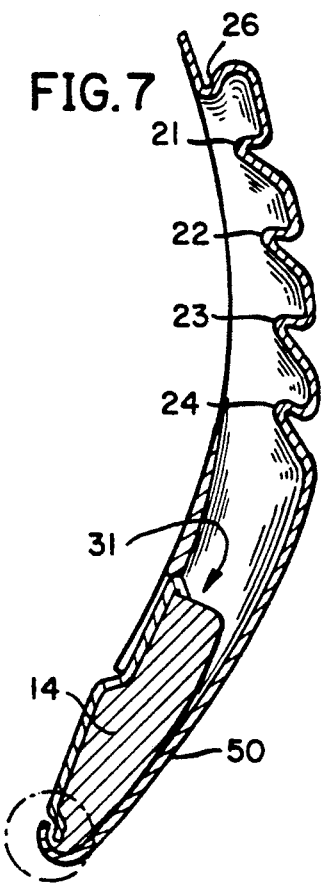
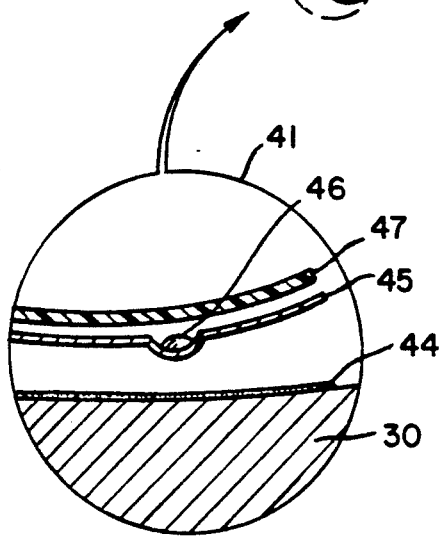

METHOD AND APPARATUS FOR OBTAINING THE CORE BODY TEMPERATURE OF AN INFANT

BACKGROUND OF THE INVENTION

1. Field of the Invention

This invention relates to A biological specimen collection and measurement device, and more particularly, concerns such a device which is employed primarily to measure the core body temperature of infants or persons without volitional bladder control.

2. Description of Related Art

Urine specimen collectors which combine sampling with the ability to measure the peak temperature of a collected sample are known in the prior art. For example, in my prior U.S. Pat. No. 4,408,905 I disclosed a device for accurately providing an instantaneous temperature reading of a collected sample using a liquid crystal display. The device shown there was developed to be fitted onto a conventional toilet and easily used to depict the changes in body temperature that occur with ovulation and pregnancy in women.

In my U.S. Pat. No. 4,564,299 I depicted another collection and measurement device which was disposable. There, I showed how such a device could be the modern equivalent of a common household oral thermometer.

However, the measurement of body temperatures using generally the techniques disclosed in these earlier patents are not readily adaptable to very young infants and to other persons with lack of bladder control. Infants, for example, are totally dependent without the ability to communicate needs and to understand directions. Furthermore, specimens are not available upon demand and infants do not have volitional bladder control. Moreover, most prior art devices require a minimum of 25 c.c. of urine, while infants, during the first month of life, will void as little as 15 c.c. of urine.

In infants particularly, an elevated temperature is an early and important sign of the onset of illness. At present, there is no easy or ideal way to take an infant's temperature. Today, the methods used are either imprecise (e.g.. body surface temperature, measured by liquid crystal thermometers, or axillary temperature as measured by electronic mercury-in-glass, chemical, and liquid crystal thermometers) or invasive (e.g.. tympanic membrane temperature, measured by infra-red thermometer or rectal temperature, measured by electronic or mercury-in-glass thermometers). The dangers associated with the use of invasive devices on very young children are well-known, as are the safety concerns associated with oral temperature reading devices.

Accordingly, it is an object of this invention to provide a device for measuring core body temperature of infants accurately and without discomfort.

It is another object of this invention to provide a means for measuring core body temperatures in individuals without volitional bladder control, such as infants, and with a minimal urine volume.

It is yet another object of this invention to provide a disposable device for measuring urinary temperatures which will accurately and efficiently provide a measurement of core body temperature in infants.

It is still another object of this device to provide a means for retaining collected urine and for measuring the temperature of the collected specimen when the donor is in a reclined position.

These and other objects will become readily apparent with reference to the drawings and the following description wherein:

SUMMARY OF THE INVENTION

This invention concerns a novel device for measuring core body temperature of infants; individuals without volitional bladder control and in situations where there is a minimal urine volume. The device combines in a single structure a collecting reservoir having a gelling agent for absorbing and immobilizing urine and a peak temperature detecting sensor thermally in contact with the immobilized urine. A feature of this invention is a urine collection system built into the device incorporating a plurality of ribbed surfaces and a cooperating peripheral gutter for channeling the urine into the reservoir. Importantly, the ribbed surfaces resist compression of collection systems and inadvertant closure of the reservoir orifice.

BRIEF DESCRIPTION OF THE DRAWING

FIG. 1 is a front view of the specimen collection and measuring thermometer;

FIG. 2 is a rear view of thermometer depicted in FIG. 1 showing an adhesive strip for adherence to a diaper;

FIG. 3 is a cross-sectional view of the upper portion of the thermometer showing the general profile of urine collection systems with a circumferential gutter;

FIG. 4 is a cross-sectional view of sump or reservoir showing the contiguous nature and relationship of the collection system and reservoir;

FIG. 5 is a side view showing in particular the rib sections for collecting urine; the circumferential gutter and their positional relationship to the sump;

FIG. 6 is a blow-up of the bottom portion of the reservoir indicated in FIG. 7; and FIG. 7 is a cross-sectional view of the reservoir and temperature sensor.

DESCRIPTION OF THE PREFERRED EMBODIMENTS

In general terms and with reference to FIG. 1 my preferred embodiment of the collection device 10 for infants is shown therein and designed to be positioned in close proximity to the donor with the opening generally described by the numeral 11 facing the user. For convenience, the rear of the device 10 is equipped with an adhesive strip 12 which can be used to affix device 10 to a diaper (not shown) and to position device 10 to catch the urine as dispensed. Collection device 10 is provided with a superabsorbent material or powder 13 (a gelling agent) in sump or reservoir 14 to immobilize the urine for the purpose of increasing peak detecting signal time by sensor 15. In this regard a sponge (not shown) might be used as an alternative way to retain urine in contact with the sensor. For a more detailed discussion of gelling agents such as sodium polyacrylate, which may be used to absorb and immobilize urines, see U.S. Pat. Nos. 4,748,069; 4,749,600 and 4,853,266.

Concerning the specific structure of device 10 with reference initially to FIG. 1, as can be seen the urine collection system includes a series of undercut ribbing sections 21–24 shown in greater detail in cross-sectional views FIGS. 5 and 6 in opening 11. Advantageously, ribbing sections 21–24 which are a series of alternately undercut and raised surfaces constitute a framework within device 10 for resisting external compression and unwanted closure. In my preferred embodiment the entire upper assembly is formed from extruded expanded polystyrene (EPS) foam sheet or any moldable, inert, medical grade plastic foam sheet that is impermeable to urine. In addition, a foam sheet provides insulation to retain the heat within the urine for a longer period. In general terms opening 11 forms a funnel-shaped surface directed downward toward sump 14.

Continuing with the discussion of the urine collection system, as can be seen in FIG. 1, device 10 contains a circumferential gutter 25 formed by overturning edge 26 during the forming process. Gutter 25 serves to retain and direct urine within opening 11, and particularly urine collected by ribbing sections 21-24, downward into sump 14. For details of the circumferential gutter 26 reference should be made to FIGS. 5 and 6 where the structure is showed in cross-sectional views. See also FIG. 3 for another sectional view of gutter 26.

Turning next to sump or reservoir 14 with reference to FIG. 1 for the overall discussion and then to FIGS. 6 and 7, it contains a peak temperature sensor 15 readable as shown in FIG. 1; an interior surface containing a superabsorbent powder 30 (FIG. 6); and an internal framework to keep sump 14 and its orifice, generally indicated by the arrow and numeral 31, patent.

Sensor 15 may be electronic and employ a thermistor sensing device (not shown) which is connected to an external display which can be read outside a diaper containing device 10. Alternatively, sensor 15 could be a liquid crystal, for example the indicators produced by Hallcrest, Inc. of Glenview, Ill.; or by Medical Indicators of W. Trenton, N.J. In my preferred embodiment, I have chosen a chemical sensor which has a rapid response time and low thermal inertia such as the melting point thermometer manufactured by PyMaH, Inc. of Somerville, N.J.

With reference to FIG. 6 reservoir 14 can be readily seen and with specific reference to the blown-up section the structure of the temperature sensor will now be described. As previously shown and discussed with reference to FIG. 1, sensor 15 consists of a series of chemical spots or locales, e.g. locales 41-43. The detail structure for a typical locale 41-43 is shown in the blown-up section in FIG. 6. As shown there the interior of reservoir 14 includes a superabsorbent powder 30 affixed by adhesive 44 to the interior of reservoir 14. Sensor 15 comprises aluminum backer 45, a particular temperature sensitive chemical deposit 46 situated in a indent in backer 45 and a transparent mylar layer 47 through which sensor 15 can be reached. This chemical sensor operates in a well-known fashion as follows. Each chemical locale is calibrated to change color when subject to a precise temperature range. For details on sensors generally and to chemical sensors, reference should be made to U.S. Pat. Nos. 4,042,336; 4,382,063; 4,448,548; and 4,473,530 for additional details.

To maintain urine in contact with sensor 15, reservoir 14 contains an immobilizing agent which contacts the donor's urine. There are many types of materials which could be used to contain urine such as open and closed cell foams and sponges (e.g. methyl cellulose pads manufactured by Americal Corp. of Mystic, Conn.). In my preferred embodiment, I have used a superabsorbent powder 30 held in reservoir 14 in proximity to chemical sensor 15 by adhesive 44. In this way the efficiency of the reading is greatly improved even when small quantities of urine are present. Powder 30 is made from sodium polyacrylate. For a more detailed discussion on the manner in which superabsorbent gels work, see U.S. Pat. Nos. 4,748,069; 4,749,600 and 4,832,046. It should be noted particularly the use of an immobilizing agent together with the urine collection system priorly described enables a donor to utilize device 10 in a reclined posture.

Reservoir 14 resists external compression and closure due to an internal framework 50 which, as shown in FIG. 6 is positioned along the entire length of the wall of reservoir 14. In this fashion the wall does not readily collapse defeating the collection system.

Particular note should be paid to anatomic curvature of device 10. This can be best appreciated with reference to FIGS. 5 and 6 which present a side view of preformed device 10.

It will be appreciated that variations in the foregoing design can be made in the disclosed design and those variations would be within the scope and spirit of the disclosed invention. For example, device 10 could be used as a single layer diaper, applied to the perineal area and held in place with adhesive tape affixed to the skin. Alternatively, the device could be held in position by affixing a diaper to the infant over the diaper thermometer unit. Additionally, the device could be an integral internal layer of a standard size and shape disposable diaper.

Another aspect of this invention concerns means for indicating the sensor reading external to the device and to a diaper, if used. If the temperature sensor is hidden from view when applied to an infant, then urination could be detected in one of two ways. A peak-detecting temperature sensor could be used, making the temperature reading independent of the time from voiding, such as I have disclosed herein. Alternatively, to avoid having to repeatedly open and close a diaper to inspect the contents of sump 14, an indicator thread or wick extends from the interior of sump 15 to the exterior. The wick could be pH sensitive, composed of solvent-sensitive materials, or use osmolarity to detect the presence of urine.

What I claim is:

1. A device for measuring core body temperature of individuals without volitional bladder control from a freshly voided urine specimen comprising:
   a sump having a viewable temperature indicator;
   an impermeable insulating barrier for collecting and directing urine into said sump,
   means for immobilizing the urine contained in said sump to increase the peak detecting signal time of said temperature sensor, and
   wherein said sump incorporates a structural framework to prevent external compression from closing its orifice.

2. A device for measuring core body temperature of infants and incontinent adults from a freshly voided urine specimen comprising:
   an anatomic conforming impermeable insulating barrier for directing the flow of urine:
   a sump attached to said insulating barrier to collect said urine flow; means supporting an opening of said sump to resist closure as a result of external compression,
   a temperature sensing element in contact with said collected urine for indicating the peak temperature of the urine and thereby the core body temperature, and means for immobilizing said urine.

3. The invention disclosed in claim 2 wherein said insulating barrier contains a circumferentially disposed gutter, a plurality of raised rib surfaces for directing the urine flow into said gutter, and said gutter being oriented to drain into said sump.

4. The invention disclosed in claim 2 wherein said immobilizing means is situated within said sump for concentrating the collected urine to accelerate the peak detection response time of said element.

5. The invention claimed in claim 4 wherein said immobilizing means consists of sodium polyacrylate which reacts with said collected urine to form a gel-like material.

6. A disposable non-invasive thermometer for measuring urine temperature comprising:

a moldable impermeable barrier having at one end a relatively open surface for collecting voided urine and at its contiguous opposite end a closed area forming a reservoir having an opening facing said open surface into which the collected urine can be channelled, superabsorbent means within said reservoir for containing urine channelled into said reservoir opening, a temperature sensor in contact with said superabsorbent means for providing a peak temperature indication representative of the infant's whole body temperature, and, a framework within said reservoir to resist external compression and closure.

7. The invention recited in claim 6 wherein said barrier has raised rib surfaces connected to a circumferentially oriented gutter on said relatively open surface to concentrate and direct collected urine into said reservoir.

8. A disposable non-invasive thermometer for measuring voided urine temperature comprising:

a moldable impermeable barrier having at one end a relatively open surface for collecting voided urine and at its contiguous opposite end a closed area forming a reservoir having an opening facing said open surface into which the collected urine can be channeled, a temperature sensor in contact with said collected urine for providing a peak temperature indication, a plurality of undercut ribs on said open surface oriented to direct said voided urine into said reservoir, a circumferentially disposed gutter on said barrier cooperating with said ribs to direct voided urine flow and means for immobilizing said urine.

* * * * *